United States Patent [19]

Escobar et al.

[11] Patent Number: 4,579,867

[45] Date of Patent: Apr. 1, 1986

[54] STABLE PHARMACEUTICAL COMPOSITIONS OF SHORT-ACTING β-ADRENERGIC RECEPTOR BLOCKING AGENTS

[75] Inventors: Agustin Escobar, Aguadilla, P.R.; Dietmar M. Wagenknecht, Zion; Abu S. Alam, Libertyville, both of Ill.

[73] Assignee: American Hospital Supply Corporation, Evanston, Ill.

[21] Appl. No.: 598,131

[22] Filed: Apr. 9, 1984

[51] Int. Cl.$^4$ ............ A61K 31/235; A61K 31/405; A61K 31/275; A61K 31/24

[52] U.S. Cl. .................................. 514/544; 514/415; 514/419; 514/522; 514/533; 514/534; 514/535; 514/538

[58] Field of Search ............... 514/544, 415, 419, 522, 514/533, 534, 535, 538; 424/308

[56] References Cited

U.S. PATENT DOCUMENTS

| | | | |
|---|---|---|---|
| 1,476,934 | 12/1923 | Volwiler et al. | 560/110 |
| 3,501,769 | 3/1970 | Crowther et al. | 560/110 |
| 4,387,103 | 6/1983 | Erhardt et al. | 560/110 |
| 4,402,974 | 9/1983 | Matier et al. | 424/308 |
| 4,405,642 | 9/1983 | Kam et al. | 560/110 |

FOREIGN PATENT DOCUMENTS

| | | | |
|---|---|---|---|
| 22464 | 3/1973 | Japan | 549/120 |
| 22465 | 3/1973 | Japan | 549/120 |

OTHER PUBLICATIONS

J. Cardiovascular Pharmacol. 6:555–564 (1984)—Gorczynski et al.
Tatsuno et al.-J. Med. Chem., vol. 20, No. 3, pp. 394–397 (1977).
Howe, J. Med. Chem., 11:1000–1008 (1968).
Frishman,-Amer. Heart J. 99, 528–536 (1980).
Kenakin; Can. J. Physiol. Pharmacol. 60, 249 (1982).
Chem. Abst. 68, 76664u (1968)—Buechi et al.
Chem. Abst. 79, 18419j (1973)—Kasuya et al.
Chem. Abst. 101, 54660n (1984)—Kam et al.

Primary Examiner—Douglas W. Robinson
Attorney, Agent, or Firm—Gildo E. Fato

[57] ABSTRACT

A pharmaceutical composition for parenteral administration is disclosed which comprises from about 0.01% to about 30% of a β-adrenergic blocking compound of the formula

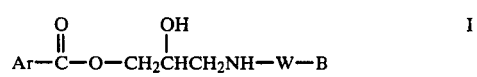

wherein Ar represents a substituted or unsubstituted aromatic group or heterocyclic group; W represents alkylene of from 1 to about 10 carbon atoms; and B represents —NR$_2$COR$_1$, —NR$_2$CONR$_1$R$_3$, —NR$_2$SO$_2$R$_1$, —NR$_2$SO$_2$NR$_2$R$_3$, or —NR$_2$COOR$_1$ wherein R$_1$, R$_2$ and R$_3$ may be the same or different and may be hydrogen, alkyl, alkoxyalkyl, cycloalkyl, alkenyl, alkynyl, aryl, heteroaryl, or aralkyl, except that R$_1$ is not hydrogen when B is —NR$_2$SO$_2$R$_1$ or —NR$_2$COOR$_1$, or R$_1$ and R$_3$ may together with N form a 5 to 7 membered heterocyclic group or W and B together denote Z which represents lower alkyl or aralkyl; or a pharmaceutically acceptable salt thereof in a hydroalcoholic solution including from about 5% to about 50% ethanol by volume of a physiologically acceptable polyhydric compound; from about 0.05 to about 2 molar physiologically acceptable buffering agent; said hydroalcoholic solution having a pH of from about 2.0 to about 4.0. The pharmaceutical compositions are useful in the treatment or prophylaxis of cardiac disorders.

35 Claims, 5 Drawing Figures

FIG. 1.

PSEUDO FIRST ORDER DEGRADATION RATE VERSUS PH COMPOUND OF FORMULA 11 0.1M, TARTARATE BUFFER 0.1M FOR 15 DAYS AT 75°C.

FIG. 2.

PSEUDO FIRST ORDER DEGRADATION RATE VERSUS TOTAL ALCOHOLIC MIXTURE (PG/ETOH): COMPOUND OF FORMULA 11 0.1M AT 75°C.

FIG. 3.

LN OF POTENCY VERSUS TIME FOR TARTARATE BUFFERED 0.1M SOLUTION OF COMPOUND OF FORMULA 11, 0.24M, PH 3 CONTAINING 15% PROPYLENE GLYCOL AND 15% ALCOHOL AT 75°C.

LN OF POTENCY VERSUS TIME FOR UNBUFFERED SOLUTION OF COMPOUND OF FORMULA 11 0.24 M CONTAINING 15% PROPYLENE GLYCOL AND 15% ALCOHOL AT 75°C.

DEGRADATION STUDY OF THE COMPOUND OF FORMULA 11 IN AQUEOUS SOLUTION AND PARENTERAL DESCRIBED FORMULATION AT VARIOUS CONDITIONS.

STABLE PHARMACEUTICAL COMPOSITIONS OF SHORT-ACTING β-ADRENERGIC RECEPTOR BLOCKING AGENTS

BACKGROUND OF THE INVENTION

The β-adrenergic receptor blocking agents comprise an important group of approved therapeutic agents. They have the common pharmacological property of blocking the action of agonists of β-adrenergic receptor sites in that they compete with the agonists for receptor sites. Various physiological responses, characteristic of the tissue which is involved, occur as a result of blocking of the receptor site. Beta-adrenergic blocking agents have a variety of pharmacokinetic properties, some of which may influence side effects. Commonly, these agents are administered to patients suffering from ischemic heart disease or myocardial infarction for the purpose of reducing the work conducted by the heart, namely heart rate and contractile force. Reducing heart work reduces oxygen demand and may in fact, increase oxygen supply. Reducing the work required of the heart can thereby minimize or prevent further tissue damage and can relieve the pain of angina pectoris.

The use of β-adrenergic receptor blocking agents to decrease myocardial oxygen requirements and control dysrhythmia after acute myocardial infarction has, however, been somewhat limited in view of the potential for producing long-lasting cardiac depression. It has therefore been suggested (Erhardt, et al, J Med Chem, 1982, Vol. 25, pp 1402–1407) that β-adrenergic blocking agents having an ultrashort duration of action could minimize or eliminate this limitation. Such agents could be administered by intravenous infusion to rapidly obtain desired levels of β-adrenergic blockade; allow rapid adjustment of blockade as might be required; and reduce the risk of resultant long-lasting cardiac depression since the effects of the agent would rapidly dissipate upon the termination of the infusion.

As described in the Erhardt, et al publication, supra as well as publications by Zaroslinski, et al, Life Sciences, Vol. 31, pp 899–907, 1982 and Erhardt, et al, J Med Chem, Vol 25, 1982, pp 1408–1412, certain compounds containing ester functions have been found to possess β-adrenergic blocking action of relatively short duration of action in vivo. Consequently, these compounds minimize the disadvantages of previous β-blocking agents. The ester groups in these compounds are however, somewhat unstable in aqueous solutions such as those used for intravenous administration. As a consequence, such solutions have a relatively short shelf life. Pharmaceutical compositions of short-acting β-blocking agents which are stable in solution and therefore have a relatively long shelf life are desirable since they would facilitate storage and commercial distribution.

SUMMARY OF THE INVENTION

The present invention is directed to stable pharmaceutical compositions for parenteral administration of compositions useful in the treatment of patients having a cardiac condition such as hypertension, angina pectoris and the like and for the treatment of arrhythmias and myocardial infarction. The compositions are particularly suited for the administration of short-acting β-adrenergic receptor blocking agents such as the (arylcarbonyloxy) propanolamines containing esters.

More specifically, the invention is directed to a pharmaceutical composition for parenteral administration comprising from about 0.01 to about 30% by weight of a β-adrenergic receptor blocking agent of the formula wherein Ar represents a substituted or unsubstituted aromatic group or heterocyclic group; W represents alkylene of from 1 to about 10 carbon atoms; and B represents $-NR_2COR_1$, $-NR_2CONR_1R_3$, $-NR_2SO_2R_1$, $NR_2SO_2NR_1R_3$, or $-NR_2COOR_1$ wherein $R_1$, $R_2$ and $R_3$ may be alike or different and may be hydrogen, alkyl, alkoxyalkyl cycloalkyl, alkenyl, alkynyl, aryl, heteroaryl, or aralkyl, except that $R_1$ is not hydrogen when B is $-NR_2SO_2R_1$ or $-NR_2COOR_1$, or $R_1$ and $R_3$ may together with N form a 5 to 7 membered heterocyclic group, or a pharmaceutically acceptable salt thereof, in a hydroalcoholic or aqueous solution which comprises from about 0.05 to about 2 molar concentration of a physiologically acceptable buffer; from about 5 to about 50% ethanol by volume; from about 5 to about 50% by volume of a physiologically acceptable liquid polyhydric compound wherein the polyhydric compound is propylene glycol, a polyethylene glycol having a molecular weight of from about 200 to about 600 daltons or glycerol; said hydroalcoholic or aqueous solution having a pH of from about 2.0 to about 4.0.

The invention will be particularly described with reference to the following compound namely N-(1,1-Dimethyl-2-ureidoethyl)-2-hydroxy-3-(O-fluorobenzoyloxy) propylamine.

The terms "loweralkyl" and "loweralkoxy" as used herein refer to straight or branched chain alkyl radicals containing from 1 to 6 carbon atoms including but not limited to methyl, ethyl, n-propyl, iso-propyl, n-butyl, sec-butyl, 2-methylhexyl, n-pentyl, 1-methylbutyl, 2,2-dimethylbutyl, 2-methylpentyl, 2,2-dimethylpropyl, n-hexyl and the like.

The term "halo" as used herein refers to chloro, bromo, fluoro and iodo.

The term "pharmaceutically acceptable salts" includes nontoxic acid addition salts of the compounds of the invention which are generally prepared by reacting the free base with a suitable organic or inorganic acid. Representative salts include the hydrochloride, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, and like salts. Also included are metallic salts such as the sodium or potassium salt of the acid.

The present compositions may be administered to warm-blooded animals parenterally. They can generally be administered with a pharmaceutical carrier. The term "pharmaceutical carrier," for the purpose of the present invention, is intended to refer to any medium that is suitable for the preparation of a parenteral dosage form, and thus includes a pharmaceutically acceptable vehicle or solvent such as is ordinarily used in the preparation of intravenous or intramuscular solutions.

A pharmaceutical composition containing the described compounds can be administered to warm-blooded animals in parenteral dosage form at the desired concentration level to achieve effective β-blocking activity for a particular disease condition. A generally effective dosage level and rate of administration is 1–500 μg/kg/minute.

DESCRIPTION OF THE DRAWINGS

In order to better understand the invention, reference can be made to the attached drawings wherein.

DETAILED DESCRIPTION OF THE INVENTION

In accordance with the present invention, it has been discovered that a stable pharmaceutical composition having a relatively long shelf life can be prepared using short-acting, ester-containing β-adrenergic receptor blocking agents such as (arylcarbonyloxy) propanolamines.

More specifically, the invention is directed to a pharmaceutical composition for parenteral administration comprising from about 0.01 to about 30% by weight of a β-adrenergic receptor blocking agent of the formula

I wherein Ar represents a substituted or unsubstituted aromatic group, including monocyclic, polycyclic and heterocyclic ring systems; W represents a straight or branched chain alkylene of from 1 to about 10 carbon atoms; and B represents —NR$_2$COR$_1$, —NR$_2$CONR$_1$R$_3$, —NR$_2$SO$_2$R$_1$, —NR$_2$SO$_2$NR$_1$R$_3$, or —NR$_2$COOR, wherein R$_1$, R$_2$ and R$_3$ may be the same or different and may be hydrogen, alkyl, of from 1 to about 10 carbon atoms, alkoxyalkyl wherein the alkyl groups may be the same or different and contain from 1 to about 10 carbon atoms, cycloalkyl of from 3 to about 8 carbon atoms, alkenyl of from 3 to about 10 carbon atoms, alkynyl of from 3 to about 10 carbon atoms, aryl which includes monocyclic or polycyclic aromatic or heterocyclic ring systems of from 2 to about 10 carbon atoms such as phenyl, thiophenyl, imidazole, oxazole, indole, and the like, aralkyl wherein the alkyl group contains from about 1 to about 6 carbon atoms and the aryl group represents substituted or unsubstituted monocyclic or polycyclic aromatic or heterocyclic ring systems of from 2 to about 10 carbon atoms, such as benzyl, phenethyl, 3,4-dimethoxyphenethyl, 1,1-dimethyl-2-(3-indolyl)-ethyl and the like, except that R$_1$ is not hydrogen when B is —NR$_2$SO$_2$R$_1$ or —NR$_2$COOR$_1$, or R$_1$ and R$_3$ may together with N form a 5 to 7 membered heterocyclic group, such as pyrrolidine, piperidine, piperazine, morpholine or thiomorpholine, or W and B together denote Z which represents lower alkyl or aralkyl. Aromatic (Ar) substituents may include lower alkyl of from 1 to about 10 carbon atoms, alkenyl of from 2 to about 10 carbon atoms, alkynyl of from 2 to about 10 carbon atoms, alkoxy wherein the alkyl group contains from 1 to about 10 carbon atoms, halogen, acetamido, amino, nitro, alkylamino of from 1 to about 10 carbon atoms, hydroxy, hydroxyalkyl of from 1 to about 10 carbon atoms, cyano, arylalkoxy wherein the alkyl group contains from 1 to about 6 carbon atoms and the aryl group represents substituted or unsubstituted phenyl and groups of the formula wherein R$_4$ is lower alkyl, aryl or aralkyl and A is a direct bond, alkylene of from 1 to about 10 carbon atoms or alkenylene of from 2 to about 10 carbon atoms or a pharmaceutically acceptable salt thereof. The β-blocking agent is contained in a hydroalcoholic or aqueous solution which comprises from about 0.05 to about 2 molar concentration of a physiologically acceptable buffer; from about 5 to about 50% ethanol by volume; from about 5 to about 50% by volume of a physiologically acceptable liquid polyhydric compound wherein the polyhydric compound is propylene glycol, a polyethylene glycol having a molecular weight of from about 200 to about 600 daltons or glycerol; said hydroalcoholic or aqueous solution having a pH of from about 2.0 to about 4.0.

Included in the present invention are pharmaceutical compositions including compounds of the formula

I wherein Ar represents an aromatic group which may be unsubstituted or substituted with alkyl of from 1 to about 6 carbon atoms, alkenyl of from 2 to about 6 carbon atoms, alkynyl of from 2 to about 10 carbon atoms, alkoxy wherein the alkyl group contains from 1 to about 6 carbon atoms, halogen, acetamido, amino, nitro, alkylamino of from 1 to about 6 carbon atoms, hydroxy, hydroxyalkyl of from 1 to about 6 carbon atoms, cyano or arylalkoxy wherein the alkyl group contains from 1 to about 6 carbon atoms and the aryl group is substituted or unsubstituted phenyl; W represents alkylene of from 1 to about 10 carbon atoms; and B represents —NR$_2$COR$_1$, —NR$_2$CONR$_1$R$_3$, —NR$_2$SO$_2$R$_1$, —NR$_2$SO$_2$NR$_1$R$_3$, or —NR$_2$COOR$_1$ wherein R$_1$, R$_2$ and R$_3$ may be the same or different and represent hydrogen, alkyl of from 1 to about 6 carbon atoms, alkoxyalkyl wherein the alkyl groups may be the same or different and contain from 1 to about 6 carbon atoms, cycloalkyl of from 3 to about 8 carbon atoms, alkenyl of from 2 to about 6 carbon atoms, alkynyl of from 2 to about 6 carbon atoms, aralkyl wherein the alkyl group contains from 1 to about 6 carbon atoms and the aryl group represents substituted or unsubstituted monocyclic or polycyclic aromatic or heterocyclic ring systems of from 2 to about 10 carbon atoms, or a substituted or unsubstituted aromatic or heterocyclic group of from 2 to about 10 carbon atoms wherein the substitutent groups may be alkyl of from 1 to about 6 carbon atoms, except that $R_1$ is not hydrogen when B is $-NR_2SO_2R_1$ or $-NR_2COOR_1$, or $R_1$ and $R_3$ may together with N form a 5 to 7 membered heterocyclic group; and the pharmaceutically acceptable salts thereof.

The present invention also includes pharmaceutical compositions including compounds of the formula wherein Ar represents phenyl which is unsubstituted or substituted with alkyl of from 1 to about 6 carbon atoms, alkoxy wherein the alkyl group contains from 1 to about 4 carbon atoms, halogen, hydroxy, nitro, amino, phenoxy, or benzyloxy; W represents alkylene of from 1 to about 6 carbon atoms; and B represents $-NR_2COR_1$, $-NR_2CONR_1R_3$, $-NR_2SO_2R_1$, $-NR_2SO_2NR_1R_3$, or $-NR_2COOR_1$, wherein $R_1$, $R_2$ and $R_3$ may be the same or different and represent hydrogen, alkyl of from 1 to about 6 carbon atoms, alkoxyalkyl wherein the alkyl groups may be the same or different and contain from 1 to about 6 carbon atoms, cycloalkyl of from 3 to about 8 carbon atoms, a substituted or unsubstituted aryl group of from 5 to about 6 carbon atoms, or a 5 to 7 membered heterocyclic group, except that $R_1$ is not hydrogen when B is $-NR_2SO_2R_1$ or $-NR_2COOR_1$, or $R_1$ and $R_3$ may together with N form a 5 to 7 membered heterocyclic group; and the pharmaceutically acceptable salts thereof.

Additionally the present invention includes pharmaceutical compositions including compounds of the formula wherein $X_1$, $X_2$ and $X_3$ may be the same or different and represent hydrogen, halogen, hydroxy, hydroxyalkyl of from 1 to about 6 carbon atoms, nitro, amino, alkyl of from 1 to about 6 carbon atoms, phenoxy benzyloxy, or alkoxy wherein the alkyl group contains from 1 to about 4 carbon atoms; W represents alkylene of from 1 to about 6 carbon atoms; and B represents $-NR_2COR_1$, $-NR_2CONR_1R_3$, $-NR_2SO_2R_1$, $-NR_2SO_2NR_1R_3$, or $-NR_2COOR_1$ wherein $R_1$, $R_2$, and $R_3$ may be the same or different and represent hydrogen, alkyl of from 1 to about 6 carbon atoms, alkoxyalkyl wherein the alkyl groups may be the same or different and contain from 1 to about 6 carbon atoms, cycloalkyl of from 3 to about 8 carbon atoms, phenyl, benzyl, or a 5 to 7 membered heterocyclic group, except that $R_1$ is not hydrogen when B is $-NR_2SO_2R_1$ or $-NR_2COOR_1$, or $R_1$ and $R_3$ may together with N form a 5 to 7 membered heterocyclic group; and the pharmaceutically acceptable salts thereof.

Preferred compositions are those including compounds of the present invention of the formula wherein, $X_1$, $X_2$ and $X_3$ may be the same or different and represent hydrogen, halogen, hydroxy, hydroxyalkyl of from 1 to about 6 carbon atoms, nitro, amino, benzyloxy, phenoxy, alkyl containing from 1 to about 6 carbon atoms, or alkoxy wherein the alkyl group contains from 1 to about 6 carbon atoms; W represents ethylene, 1-methylethylene, or 1,1-dimethylethylene, and Y is $-COR_1$, $-CONR_1R_3$, $-SO_2R_1$, $-SO_2NR_1R_3$, or $-COOR_1$, wherein $R_1$ and $R_3$ may be the same or different and may be hydrogen, alkyl containing from 1 to about 6 carbon atoms, alkoxyalkyl wherein the alkyl groups may be the same or different and contain from 1 to about 6 carbon atoms, substituted or unsubstituted phenyl, substituted or unsubstituted heterocyclic group of from 2 to about 10 carbon atoms, aralkyl wherein the alkyl group contains from 1 to about 6 carbon atoms and the aryl group represents substituted or unsubstituted phenyl, or a heterocyclic group of from 2 to about 10 carbon atoms, except that $R_1$ is not hydrogen when Y is $-SO_2R_1$ or $COOR_1$, or $R_1$ and $R_3$ may together with N form a 5 to 7 membered heterocyclic group; and the pharmaceutically acceptable salts thereof.

Particularly preferred compositions are those including compounds of the following formulae wherein $X_1$, $X_2$ and $X_3$ may be the same or different and represent hydrogen, halogen, hydroxy, nitro, amino, alkyl of from 1 to about 4 carbon atoms, or benzyloxy; W represents alkylene of from 1 to about 6 carbon atoms; and $R_1$ represents alkyl of from 1 to about 6 carbon atoms, alkoxyalkyl wherein the alkyl groups may the same or different and contain from 1 to about 4 carbon atoms, cycloalkyl of from 3 to about 8 carbon atoms, phenyl, benzyl, or a 5 to 7 membered heterocyclic group; and the pharmaceutically acceptable salts thereof.

wherein $X_1$, $X_2$ and $X_3$ may be the same or different and represent hydrogen, halogen, hydroxy, nitro, amino, alkyl of from 1 to about 4 carbon atoms, or benzyloxy;

W represents alkylene of from 1 to about 6 carbon atoms; and $R_1$ and $R_3$ may be the same or different and represent hydrogen, alkyl of from 1 to about 6 carbon atoms, alkoxyalkyl wherein the alkyl groups may be the same or different and contain from 1 to about 4 carbon atoms, cycloalkyl of from 3 to about 8 carbon atoms, phenyl, or benzyl, or $R_1$ and $R_3$ may together with N form a 5 to 7 membered heterocyclic group; and the pharmaceutically acceptable salts thereof.

(c)      VIII wherein $X_1$, $X_2$ and $X_3$ may be the same or different and represent hydrogen, halogen, hydroxy, nitro, amino, alkyl of from 1 to about 4 carbon atoms, or benzyloxy; W represents alkylene of from 1 to about 6 carbon atoms; and $R_1$ represents alkyl of from 1 to about 6 carbon atoms, alkoxyalkyl wherein the alkyl groups may be the same or different and contain from 1 to about 4 carbon atoms, cycloalkyl of from 3 to about 8 carbon atoms, phenyl, benzyl, or a 5 to 7 membered heterocyclic group; and the pharmaceutically acceptable salts thereof.

(d)      IX wherein $X_1$, $X_2$ and $X_3$ may be the same or different and represent hydrogen, halogen, hydroxy, nitro, amino, alkyl of from 1 to about 4 carbon atoms, or benzyloxy; W represents alkylene of from 1 to about 6 carbon atoms; and $R_1$ and $R_3$ may be the same or different and represent hydrogen, alkyl of from 1 to about 6 carbon atoms, alkoxyalkyl wherein the alkyl groups may be the same or different and contain from 1 to about 4 carbon atoms, cycloalkyl of from 3 to about 8 carbon atoms, phenyl, benzyl, or $R_1$ and $R_3$ may together with N form a 5 to 7 membered heterocyclic group; and the pharmaceutically acceptable salts thereof.

(e)      X wherein $X_1$, $X_2$ and $X_3$ may be the same or different and represent hydrogen, halogen, hydroxy, nitro, amino, alkyl of from 1 to about 4 carbon atoms, or benzyloxy; W represents alkylene of from 1 to about 6 carbon atoms; and $R_1$ represents alkyl of from 1 to about 6 carbon atoms, alkoxyalkyl wherein the alkyl groups may be the same or different and contain from 1 to about 4 carbon atoms, and the pharmaceutically acceptable salts thereof.

Compounds of the present invention exist as two sterioisomers due to the presence of an asymmetric carbon atom. The present invention includes either stereoisomeric form as well as racemic mixtures. For compounds in which $R_1$, $R_2$ or $R_3$ represent alkenyl, both cis and trans isomers are within the scope of the invention. For compounds in which Ar is a substituted aromatic ring, the substituents may be in the ortho, meta or para positions to the propoxy carbonyl side-chain.

The compounds described herein may be prepared by any available procedure. Compounds prepared as the acid addition salts may be converted to the free base by reaction with an appropriate base such as sodium carbonate or sodium bicarbonate. Preparation of specific compounds used in the pharmaceutical compositions of the present invention is described in co-pending U.S. application Ser. No. 320,773; filed Nov. 12, 1981.

The compounds described herein are not limited to any particular stereoisomeric configuration. Such compounds may be administered as their pharmaceutically acceptable acid addition salts, e.g., as the hydrochloride, sulfate, phosphate, gluconate, tartrate, etc.

Compounds in accordance with the present invention exist as two stereoisomers due to the presence of an asymmetric carbon atom. This invention includes either stereoisomeric form, as well as racemic mixtures. Chiral compounds can be prepared by classical resolution according to the method described in U.S. Pat. No. 4,076,939. Alternatively, the chiral compounds can be prepared by asymmetric synthesis procedures.

In preferred compositions, the $\beta$-blocking agent incorporated in the pharmaceutical composition is selected from one of the following compounds.

| Compound | $X_1$ | $X_2$ | $X_3$ | W | $R_1$ | $R_3$ |
|---|---|---|---|---|---|---|
| COMPOUNDS OF FORMULA VI: | | | | | | |
| 1 | H | H | F | —CH$_2$CH$_2$ | —CH(CH$_3$)$_2$ | |
| 2 | H | H | F | —C(CH$_3$)$_2$CH$_2$— | (morpholino-O ring) | |
| 3 | H | H | F | —CH(CH$_3$)CH$_2$— | —CH$_3$ | |
| 4 | H | H | F | —C(CH$_3$)$_2$CH$_2$— | —CH$_3$ | |
| 5 | H | H | F | —C(CH$_3$)$_2$CH$_2$— | —CH(CH$_3$)$_2$.(HOOC).H$_2$O | |

-continued

| Compound | $X_1$ | $X_2$ | $X_3$ | W | $R_1$ | $R_3$ |
|---|---|---|---|---|---|---|
| 6 | H | H | F | $-C(CH_3)_2CH_2-$ | -cyclohexyl .$(HOOC)_2$ | |
| 7 | H | H | F | $-C(CH_3)_2CH_2-$ | -cyclohexyl .HCl | |
| 8 | H | H | F | $-CH_2CH_2-$ | $-CH_2-$cyclohexyl | |
| 9 | H | H | F | $-(CH_2)_2CH_2-$ | $-O(CH_2)_2OCH_3$.$(HOOC)_2$ | |
| 10 | H | H | H | $-C(CH_3)_2CH_2-$ | $-N\underset{\_\_\_}{\frown}O$.$(HOOC)_2$ | |
| 11 | H | H | Cl | $-C(CH_2)_2CH_2-$ | $-N\underset{\_\_\_}{\frown}O$.$(HOOC)_2$ | |
| 12 | 3-OH | 4-OH | H | $-(CH_3)_2CH_2-$ | $-N\underset{\_\_\_}{\frown}O$.$(HOOC).2$ | |
| 13 | 4-OH⁻ | H | H | $-C(CH_3)_2CH_2-$ | $-N\underset{\_\_\_}{\frown}O$.$(HOOC)_2$ | |
| 14 | 2-CH₃ | 4-OH | H | $-C(CH_3)_2CH_2-$ | $-N\underset{\_\_\_}{\frown}O$.$(HOOC)_2$ | |
| 15 | 3-OH | 5-OH | H | $-C(CH_3)_2CH_2-$ | $-N\underset{\_\_\_}{\frown}O$.$(HOOC)_2$.½$H_2O$ | |
| 16 | 4-NH₂ | H | H | $-C(CH_3)_2CH_2-$ | $-N\underset{\_\_\_}{\frown}O$ | |
| COMPOUNDS OF FORMULA VII: | | | | | | |
| 17 | H | H | F | $-C(CH_3)_2CH_2-$ | H | H |
| 18 | H | H | F | $-C(CH_3)_2CH_2-$ | H | $-CH_3$ |
| 19 | H | H | F | $-C(CH_3)_2CH_2-$ | H |  |
| COMPOUND OF FORMULA IX: | | | | | | |
| 20 | H | H | F | $-C(CH_3)_2CH_2-$ | $-CH_3$ | $-CH_3$ |
| COMPOUND OF FORMULA X: | | | | | | |
| 21 | H | H | F | $-C(CH_3)_2CH_2-$ | $-C_2H_5$ | |

These compounds are active β-blocking agents as illustrated by the following data of duration and potency.

The duration of β-blockade was determined in vivo using pentobarbital-anesthetized dogs instrumented for measurement of heart rate using a Beckman cardiotachometer triggered electronically by a phasic aortic blood pressure signal. Both vagus nerves were severed in the cervical region and the animals were mechanically ventilated. The experimental design used employed a 3-hour infusion of test compound. Bolus doses of isoproterenol (0.5 μg/kg) were used to assess the degree of β-blockade and recovery from β-blockade after determination of the infusion. The doses were spaced at 10-minute intervals and were given before, during and following the infusion of test compounds. The infusion rate was adjusted so that at the end of the 3-hour infusion period the degree of isoproterenol inhibition averaged about 50% of control. Following termination of blocker infusion, percent recovery from β-blockade was computed and the time associated with 80% recovery estimated. The results are contained in Table I.

TABLE 1

β-Blocking Activity In Vivo

| Compound | Potency (mg/kg/180 min) | % I[a] | Recovery Time (min) 50% | 80% | N[b] |
|---|---|---|---|---|---|
| 4 | 2.7 | 61 | 7 | 35 | 2 |
| 5 | 0.6 | 62 ± 5 | 10 ± 2 | 22 ± 6[c] | 6 |
| 6 | 1.4 | 61 | 8 ± 3 | 12 ± 3 | 3 |
| 7 | 1.8 | 68 | 8 | 19 | 1 |
| 8 | 10.3/21.9 | 43/55 | 3,4 | 6/36 | 2 |
| 21 | 6.5 ± 1.8 | 49 ± 4 | 3 ± 1 | 8 ± 3 | 3 |
| 17 | 0.7 | 49 | | 21 | 2 |
| 12 | 0.08 | 95 | >60 | >60 | 1 |
| Propranolol | 0.2 | 67 ± 6 | >60 | >60 | 2 |

[a]Percent inhibition of heart rate response to isoproterenol
[b]Number of experiments
[c]2/6 experiments did not recover to 80% within 60 min The compositions of the present invention consist of a hydroalcoholic solution containing an above described β-blocking compound (or its pharmaceutically acceptable salt) at a concentration of from about 0.01 to about 30% by weight. Concentrations of less than about 0.01% (weight) of the β-blocking compounds in solutions generally do not provide effective β-blocking activity at practical infusion rates, while there is generally no added benefit to having concentrations greater than about 30% (weight) of the β-blocker in solution. In particularly preferred compositions, the concentration of β-blocking compound in solution is from about 0.01 to about 10% by weight.

The hydroalcoholic solution preferably contains from about 5 to about 50% by volume ethanol. Ethanol has been found to be important in the stabilization of the β-blocking compound according to the present invention.

The hydroalcoholic solutions also preferably contain from about 5 to about 50% by volume of physiologically acceptable liquid polyhydric compound. Physiologically acceptable liquid polyhydric compounds include, but are not limited to, alkyls of from 1 to about 10 carbon atoms having two or more adjacent hydroxyl groups such as ethylene glycol, propylene glycol, glycerol and the like; polyethylene glycols having a molecular weight of from about 200 to about 600 daltons; and glycerine. Preferred liquid polyhydric compounds include alkyls of from 1 to 10 carbon atoms having two or more adjacent hydroxyl groups, and polyethylene glycols having a molecular weight of from about 200 to about 600 daltons. Glycerin is less preferred, because solutions containing it have been observed to discolor on storage at 55° C. A particularly preferred liquid polyhydric compound is propylene glycol. Liquid polyhydric compounds, in conjunction with ethanol are useful stabilizing components of the β-blocking compounds in the hydroalcoholic solution according to the present invention. In particularly preferred compositions, the volume ratio of ethanol to the liquid polyhydric compound is about 1:1.

Stability of the β-blocking compound in solution is affected by the pH of the solution. In preferred compositions, the pH of the hyroalcoholic solution ranges from about 2.0 to about 4.0. When the pH of the solution is less than about 2.0 or greater than about 4.0, degradation of the β-blocking compound was observed. In particularly preferred compositions, the pH ranges from about 2.8 to about 3.2, and in the most preferred compositions, the pH ranges from about 2.8 to about 3.0. The pH is preferably maintained by a physiologically acceptable buffering agent at a concentration of from about 0.05 to about 2 molar. Preferred buffering agents include tartrate buffers, acetate buffers, trishydroxymethylaminomethane, and the like; and amphoteric compounds such as glycine, cystine, and the like. Tartrate buffers are particularly preferred. The molar ratio of the β-blocking compound to buffering agent advantageously is about 1:1 to about 3:1.

The β-blocking compounds used in the pharmaceutical compositions of the present invention are made quite stable by the hydroalcoholic solution of the present invention. Typical compositions exhibit shelf lives from 12 months to 24 months, compared to about 1 week for the same compounds in conventional aqueous preparations. These compositions thus facilitate commercial distribution and storage of the above described short-acting ester-containing β-blockers.

The pharmaceutical compositions of the present invention are preferably added to a physiologically acceptable infusion medium to a final concentration of β-adrenergic compound as deemed necessary by the patient's condition and needs, and thereby parenterally administered to the patient.

The dosages and rates of administration of these compositions generally depend upon the patient's needs and the particular β-blocking compound employed. These dosages and rates of administration are described in U.S. Pat. No. 4,387,103 issued June 7, 1983.

In order to illustrate the manner in which the above compositions may be prepared and the properties of the compositions, reference is made to the following examples, which, however, are not meant to limit or restrict the scope of the invention in any respect.

For convenience, the invention will be exemplified with respect to the sulfate salt of the compound of formula II.

A stability indicating high pressure liquid chromatographic (HPLC) assay was developed for the compound of formula II which was suitable to monitor the compound and its degradation product(s) during the early phase of formulation studies. The method of HPLC analysis is described hereafter.

Formulation screening was conducted to determine the parameters essential for an acceptable product. Based on these data, the composition of the formulations containing both active and inactive ingredients were ascertained. Representative formulations were packaged in ampuls and placed on accelerated and room temperature stability test. At various time intervals, samples from stability stations were removed and assayed for potency of the compound. Based on the stability data, the formula composition is stable.

Initially, the solubility of the compound was determined in various vehicles. The amount dissolved was measured by HPLC (Table 2). The pKa is 8.17 and the aqueous solution is acidic (1% is about pH 1). Based on this acidic nature, a tartrate buffer was selected. It was foun that the molar ratio of active β-blocking agent to buffer was critical, 1:1 to 3:1 to stabilized product.

In order to determine the pH at which the formulation would show maximum stability, a kinetic degradation study was employed. pH of solutions ranging from 2–4, containing 0.1M each of the compound of formula II and tartrate buffer were stored at 75° C. At various time intervals, samples were taken and assayed for the compound.

The kinetic data obtained was plotted as a log of drug concentration versus time. The apparent first-order rate constants were calculated from the slopes of the linear regression lines fitted to log $(C) = \log (C_o) - 2.303$ kt where C is drug concentration at time t, Co is the initial drug concentration and k is the apparent first-order rate constant.

The kinetics of degradation of the drug at 75° C. and at various pH values was followed by monitoring the potency of the drug at different stability times. The logarithm of the potency versus time in all cases produced linear plots. The apparent first-order rate constants were calculated from the slopes of the linear regression lines (not shown) and are presented in FIG. 1.

Figure 1:
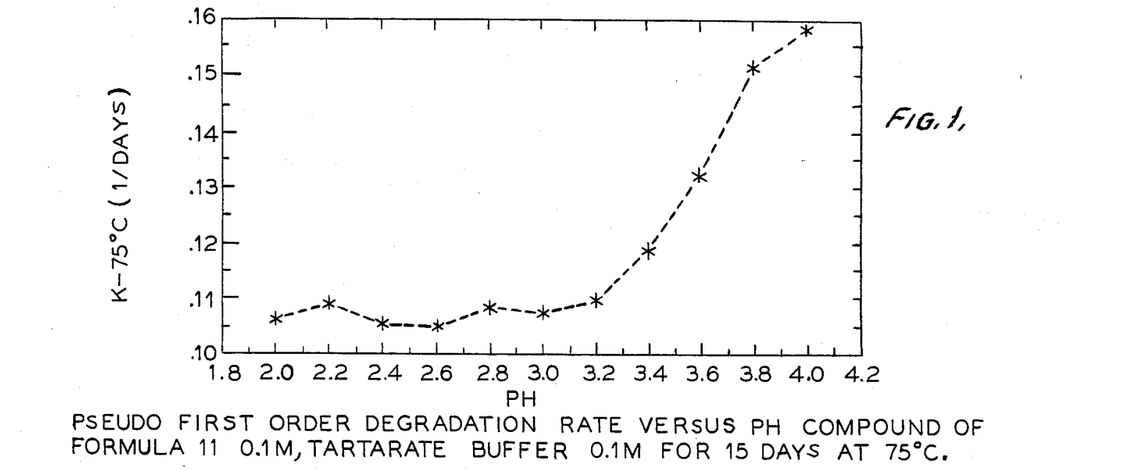
FIG. 1 is a graphic representation of the pseudo first order degradation rate versus pH for the compound of the formula II at 75° C.

The results showed a pseudo first-order degradation kinetic pattern. The pH of the stable region was determined, and considering physiological pH, a pH range of 2.8 to 3.4 was selected for formulation purpose.

Figure 2:
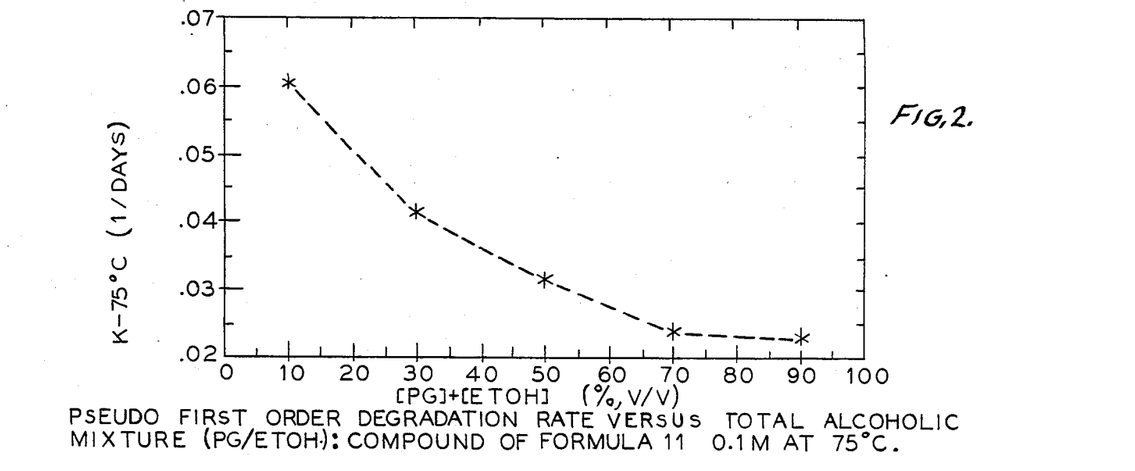
FIG. 2 is a graphic representation of the pseudo first order degradation rate versus total alcoholic mixture for the compound of formula II at 75° C.

The ratio of the two organic vehicles, namely propylene glycol and alcohol were determined by making solutions of the compound of formula II in the vehicle and testing the stability at 75° C. Samples were removed after specified times and measured for potency. The rate of degradation at various ratios of propylene glycol and alcohol were determined and plotted as shown in FIG. 2. Results point out a 1:1 ratio of the two substances minimizes degradation while at the same time not providing too high a concentration of either of them.

Figure 3:
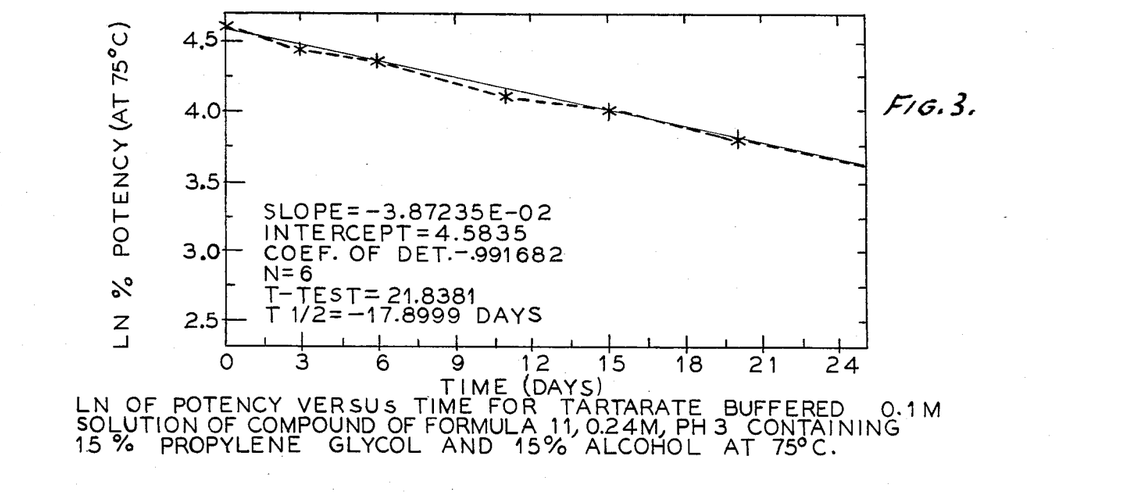
FIG. 3 is a graphic representation of the potency versus time for a buffered solution of the compound of formula II containing 15% propylene glycol and 15% alcohol at 75° C.
Figure 4:
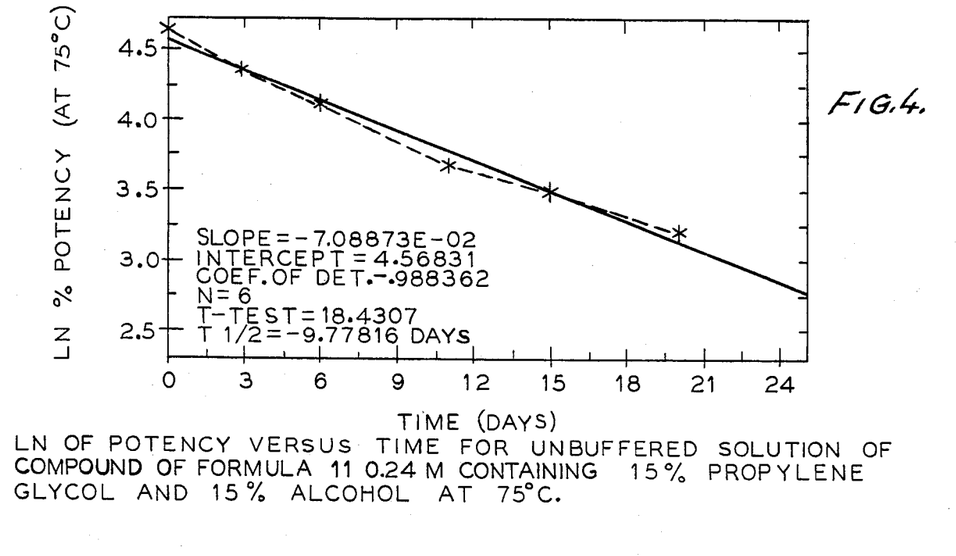
FIG. 4 is a graphic representation of the potency versus time for an unbuffered solution as described with respect to FIG. 3.

FIG. 3 illustrates the stability of the compound of formula II in hydroalcoholic solution buffered at pH 3 by sodium tartrate. An identical stability study was conducted with a solution without buffering agent (FIG. 4). Because the kinetic pattern follows pseudo first order, the potency at 75° C. upon storage was converted to natural logarithm prior to plotting. Results clearly show that the buffered preparation is approximately twice as stable as the unbuffered product. The rate of degradation as measured by the slope is $3.87 \times 10^{-2}$ day$^{-1}$ (buffered) while it is $7.09 \times 10^{-2}$ day$^{-1}$ (unbuffered).

The sulfate salt of the compound of Formula II in aqueous solution when stored at 75° C. degraded about 70% in one week. In contrast, when formulated in the pharmaceutical composition as noted and placed under the same storage conditions, it degraded only about 25%. Thus, a significant three fold increase in stability resulted when the proper composition was used to formulate the product.

Figure 5:
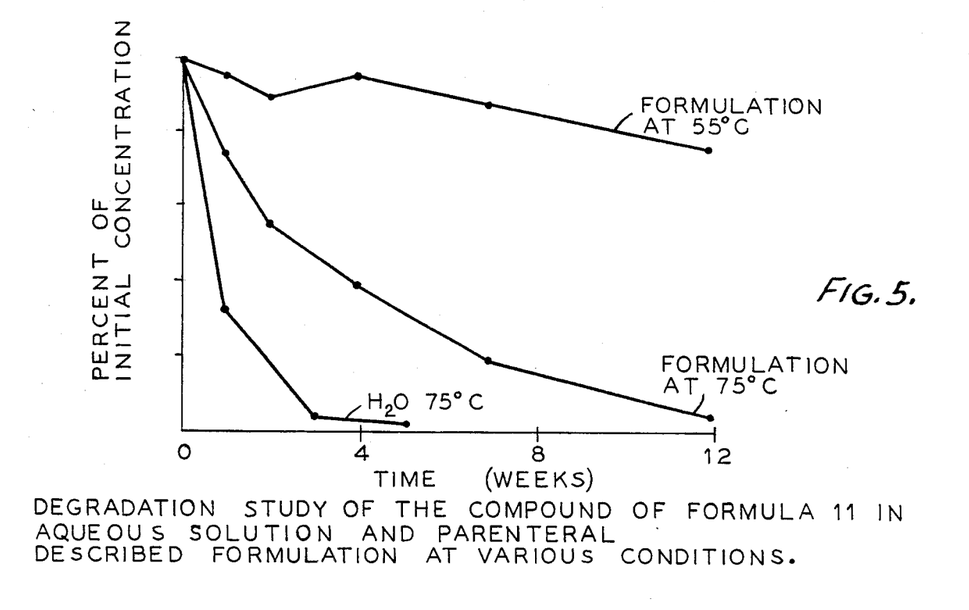
FIG. 5 is a graphic representation of a comparison of the degradation of the compound of Formula II in aqueous solution and in a pharmaceutical composition of the invention.

The results of this comparison are represented in FIG. 5. Samples for the study were prepared and tested as follows:

a. Thermal at 105° C.—A solution of the sulfate salt was prepared comprising 200 μg/mL in methanol. One mL of solution was evaporated and the residue (2 μg of the salt was placed in an oven set at 105° C. Several vials were prepared in the same manner, and removed for testing at various times. In each case, 4 mL of mobile phase was added (final conc. 50 μg/mL) for subsequent HPLC evaluation. The results are plotted as curve A in FIG. 5.

b. Aqueous at 75° C.—10 mg of sulfate salt of Formula II were dissolved in 100 mL of deionized water. A 2 mL portion of this solution was transferred to a vial and placed in a 75° C. oven. A series of vials were prepared and evaluated at various intervals. Each time 2 mL of mobile phase was added to the vial (final conc. 50 μg/mL) for subsequent HPLC evaluation. The results are plotted as curve B in FIG. 5.

c. Forced Degradation of the Formulation was carried out using a solution containing the sulfate salt of Formula II, 100 mg/mL, in Acetate Buffer (0.35M) containing 20% of Propylene Glycol:Ethanol (50:50) having a pH 3.17. The formulation solution was divided into 2 parts, placed in 55° C. and 75° C. ovens and tested periodically. To evaluate the formulation, the solution was diluted 1 mL to 100 mL of mobile phase, then 5 mL to 100 mL in mobile phase (final conc.—50 μg/mL) for subsequent HPLC evaluation.

The rates of decomposition were monitored by HPLC and compared to the respective initial concentrations at 220 nm. In order to insure that the peak was that of the sulfate salt and not an impurity, excipient or product of decomposition, the peak was scanned using a variable wavelength detector (200–300 nm). Using the Perkin-Elmer LC-75 Detector Stop Flow System described below:

A 70 μL portion of the sulfate salt degraded samples were injected manually into the HPLC L-75 equipped with a variable wavelength detector, programmed to scan wavelengths from 200 to 320 nm. When the sulfate salt reached the detector cell, the flow of mobile phase was stopped and the scan initiated from 200 to 320 nm. In this manner, only the peak corresponding to the sulfate salt was measured.

On the basis of these results, a preferred composition of formulation was selected as shown in Example 1. The formulations were packaged and placed on long-term stability. Test results are shown in Example 2. Although there were some potency losses at elevated temperatures, there were no significant losses either at room temperature, high intensity light or refrigeration.

Ordinarily, with compositions of the invention, it is preferred to experience less than a 10% potency loss at 40° C. over a three-month period or over a twelve- to twenty-four month period at room temperature. Based on the kinetic pattern at about 40° C., it is believed that a 10% potency loss at a three-month period extrapolates to a 10% potency loss at 24 months at room temperature. Without stabilization as described herein, the compound of formula II loses 10% potency within a week when stored at room temperature.

ANALYTICAL METHOD

Samples were dissolved or diluted with the mobile phase, methanol—pH 3.4 phosphate buffer solution. The resulting solutions were diluted with benzoic acid internal standard solution and chromatographed on a octadecyl silane column with detection at 229 nm. The selectivity of the chromatographic system for intact compound was demonstrated by resolving the parent drug from synthetic intermediates, potential impurities and reaction products resulting from accelerated degradation conditions. The method is linear, quantitative, rugged and reproducible with a sensitivity of 2 ug/ml.

Either peak height or peak area ratios can be used for quantitation.

TABLE 2

SOLUBILITY PROFILE OF THE SULFATE SALT OF THE COMPOUND OF FORMULA II

| Solvent | Solubility, % w/w |
|---|---|
| Water for Injection USP (WFI) | 50.70 |
| Propylene Glycol USP (PG) | 3.47 |
| Alcohol USP (EtOH) | 2.24 |
| Polyethylene Glycol 200 USP (PEG) | 2.64 |
| WFI (5%), PEG (95%) | 3.83 |
| WFI (5%), EtOH (95%) | 7.50 |
| WFI (5%), PG (95%) | 5.60 |
| WFI (5%), EtOH (45%), PG (50%) | 7.20 |
| WFI (5%), EtOH (45%), PEG (50%) | 5.21 |
| EtOH (35%), PG (35%), PEG (30%) | 4.37 |
| EFI (5%), PG (30%), PEG (30%), EtOH (35%) | 6.04 |

EXAMPLE 1

| Each 5 ml Ampul Contains: | |
|---|---|
| Salt of the Compound of Formula II | 0.25 g |
| Alcohol | 0.75 ml |
| Propylene Glycol | 0.75 ml |
| Water for Injection, q.s. to 5 ml | |

Buffer to pH 2.8-3.0 with 75 mg Tartaric Acid, Sodium Hydroxide, NF added as needed to adjust pH.
Packaging is in a 5 ml clear glass (Type 1) ampul.

The formulation is a clear, colorless, sterile, nonpyrogenic solution of the active β-blocking agent in Propylene Glycol, Alcohol, USP and Water for Injection, (15:15:70) at a concentration of 50 mg/ml.

Procedure

The ampuls and glassware for compounding, filtering and filling were washed and depyrogenated. The filter assembly, filling tube assembly and other parts and equipment were sterilized. A 10N NaOH solution was prepared. The sulfate salt of the compound of formula II and tartaric acid were weighed out and placed in a glass vessel. Water for injection (WFI) was added to dissolve the materials. The pH was adjusted to 2.9 in the aqueous phase with 10N NaOH and propylene glycol was added. The ethanol was then added and the mixture was stirred to dissolve the solid materials. Water for injection was added to the final volume and the solution was filtered through a 0.2 μm membrane. The solution was then placed in ampuls which were sealed, leak tested and inspected.

EXAMPLE 2

Ampuls prepared according to the procedure of Example 1 were selected and placed on stability test. At each stability time one ampul of each solution was removed. The pH, potency and the physical appearance of the solutions was determined. The concentration of the drug was determined by a high performance liquid chromatographic (HPLC) method. The results are tabulated in Tables 3 and 4 for 5 and 10 ml ampuls.

The glossary for the abbreviations used in the tables is as follows:
TZ—Initial, zero time
RT—Room temperature, 15°-30° C.
EL40—40° C.
EL55—55° C.
REF—Refrigerated
NL—Natural Light
IL—High intensity light, about 1200 ft. candles
W—Weeks
M—Months

TABLE 3

| Test Station Test Time | Potency Value (%) | Change | PH Value | Change | Physical Observations |
|---|---|---|---|---|---|
| ALL TZ | 100.9 | 0.0 | 3.54 | 0.000 | Clear Colorless Solution |
| RT | | | | | |
| 4W | 100.3 | −0.6 | 3.42 | −0.12 | Clear Colorless Solution |
| 3M | 101.7 | 0.8 | 3.50 | −0.04 | Clear With Faint Yellow Color |
| EL40 | | | | | |
| 4W | 95.7 | −5.2 | 3.40 | −0.14 | Clear Colorless Solution |
| 3M | 83.3 | −12.6 | 3.50 | −0.04 | Clear With Faint Yellow Color |
| EL55 | | | | | |
| 2W | 95.2 | −5.7 | 3.52 | −0.02 | Clear Colorless Solution |
| 4W | 85.3 | −15.6 | 3.43 | −0.11 | Clear Colorless Solution |
| 2M | 76.1 | −24.8 | 3.43 | −0.11 | Clear Colorless Solution |
| 3M | 65.7 | −35.2 | 3.50 | −0.04 | Clear With Faint Yellow Color |
| REF | | | | | |
| 3M | 101.0 | 0.1 | 3.53 | −0.01 | Clear With Faint Yellow Color |
| NL | | | | | |
| 3M | 102.4 | 1.5 | 3.51 | −0.03 | Clear With Faint Yellow Color |
| IL | | | | | |
| 2W | 101.1 | 0.2 | 3.52 | −0.02 | Clear Colorless Solution |

TABLE 4

Container Size: 10 ML

| Test Station Test Time | Potency Value (%) | Change | PH Value | Change | Physical Observations |
|---|---|---|---|---|---|
| ALL | | | | | |

TABLE 4-continued

| Test Station Test Time | Potency Value (%) | Change | PH Value | Change | Physical Observations |
|---|---|---|---|---|---|
| TZ | 104.5 | 0.0 | 3.57 | 0.00 | Clear Colorless Solution REF-757-25 |
| RT | | | | | |
| 4W | 101.7 | −2.3 | 3.44 | −0.13 | Clear Colorless Solution |
| 3M | 101.3 | −3.2 | 3.48 | −0.09 | Clear With Faint Yellow Color |
| EL40 | | | | | |
| 4W | 99.2 | −5.3 | 3.41 | −0.16 | Clear Colorless Solution |
| 3M | 93.9 | −10.6 | 3.48 | −0.09 | Clear With Faint Yellow Color |
| EL55 | | | | | |
| 2W | 95.7 | −8.8 | 3.56 | −0.01 | Clear Colorless Solution |
| 4W | 86.3 | −18.2 | 3.42 | −0.15 | Clear Colorless Solution |
| 2M | 77.3 | −27.2 | 3.45 | −0.12 | |
| 3M | 62.6 | −41.9 | 3.49 | −0.08 | Clear With Faint Yellow Color |
| REF | | | | | |
| 3M | 104.7 | 0.2 | 3.47 | −0.10 | Clear With Faint Yellow Color |
| NL | | | | | |
| 3M | 103.2 | −1.3 | 3.47 | −0.10 | Clear With Faint Yellow Color |
| IL | | | | | |
| 2W | 103.1 | −1.4 | 3.53 | −0.02 | Clear Colorless Solution |

What we claim is:

1. A pharmaceutical composition useful in the treatment of cardiac conditions for parenteral administration comprising from about 0.01% to about 30% of a $\beta$-adrenergic blocking compound of the formula

I wherein Ar represents a phenyl or naphthyl group which may be unsubstituted or substituted with alkyl of from 1 to about 6 carbon atoms, alkenyl of from 2 to about 6 carbon atoms, alkynyl of from 2 to about 10 carbon atoms, alkoxy wherein the alkyl group contains from 1 to about 6 carbon atoms, halogen, acetamido, amino, nitro, alkylamino of from 1 to about 6 carbon atoms, hydroxy, hydroxyalkyl of from 1 to about 6 carbon atoms, cyano or arylalkoxy wherein the alkyl group contains from 1 to about 6 carbon atoms and the aryl group is substituted or unsubstituted phenyl; W represents alkylene of from 1 to about 10 carbon atoms; and B represents $-NR_2COR_1$, $-NR_2CONR_1R_3$, $-NR_2SO_2R_1$, $-NR_2SO_2NR_1R_3$, or $-NR_2COOR_1$ wherein $R_1$, $R_2$ and $R_3$ may be the same or different and represent hydrogen, alkyl of from 1 to about 6 carbon atoms, alkoxyalkyl wherein the alkyl groups may be the same or different and contain from 1 to about 6 carbon atoms, cycloalkyl of from 3 to about 8 carbon atoms, alkenyl of from 2 to about 6 carbon atoms, alkynyl of from 2 to about 6 carbon atoms, benzyl, phenethyl, 3,4-dimethoxyphenethyl, 1,1-dimethyl-2-(3-indolyl)-ethyl, or a substituted or unsubstituted phenyl, thiophenyl, or indole group, except that $R_1$ is not hydrogen when B is $-NR_2SO_2R_1$ or $-NR_2COOR_1$; or a pharmaceutically acceptable salt thereof in a hydroalcoholic solution including from about 5% to about 50% ethanol by volume, 5% to about 50% by volume of a physiologically acceptable polyhydric compound; from about 0.05 to about 2 molar physiologically acceptable buffering agent; said hydroalcoholic solution having a pH of from about 2.0 to about 4.0.

2. A pharmaceutical composition useful in the treatment of cardiac conditions for parenteral administration comprising from about 0.01% to about 30% of a $\beta$-adrenergic blocking compound according to claim 1 of the formula

IV wherein $X_1$, $X_2$ and $X_3$ may be the same or different and represent hydrogen, halogen, hydroxy, hydroxyalkyl of from 1 to about 6 carbon atoms, nitro, amino, alkyl of from 1 to about 6 carbon atoms, phenoxy, benzyloxy, or alkoxy wherein the alkyl group contains from 1 to about 4 carbon atoms; W represents alkylene of from 1 to about 6 carbon atoms; and B represents $-NR_2COR_1$, $-NR_2CONR_1R_3$, $-NR_2SO_2R_1$, $-NR_2SO_2NR_1R_3$, or $-NR_2COOR_1$ wherein $R_1$, $R_2$, and $R_3$ may be the same or different and represent alkyl of from 1 to about 6 carbon atoms, alkoxyalkyl wherein the alkyl groups may be the same or different and contain from 1 to about 6 carbon atoms, cycloalkyl of from 3 to about 8 carbon atoms, phenyl, benzyl, or a thiophenyl, or indole group, except that $R_1$ is not hydrogen when B is $-NR_2SO_2R_1$ or $-NR_2COOR_1$; or a pharmaceutically acceptable salt thereof in a hydroalcoholic solution including from about 5% to about 50% ethanol by volume, 5% to about 50% by volume of a physiologically acceptable polyhydric compound; from about 0.05 to about 2 molar physiologically acceptable buffering agent; said hydroalcohol solution having a pH of from about 2.0 to about 4.0.

3. A pharmaceutical composition useful in the treatment of cardiac conditions for parenteral administration comprising from about 0.01% to about 30% of a $\beta$-adrenergic blocking compound according to claim 1, of the formula

V wherein $X_1$, $X_2$ and $X_3$ may be the same or different and represent hydrogen, halogen, hydroxy, hydroxyalkyl of from 1 to about 6 carbon atoms, nitro, amino, benzyloxy, phenoxy, alkyl containing from 1 to about 6 carbon atoms, or alkoxy wherein the alkyl group contains from 1 to about 6 carbon atoms; W represents ethylene, 1-methylethylene, or 1,1-dimethylethylene, and Y is $-COR_1$, $-CONR_1R_3$, $-SO_2R_1$, $-SO_2NR_1R_3$, or $-COOR_1$, wherein $R_1$ and $R_3$ may be the same or different and may be hydrogen, alkyl containing from 1 to about 6 carbon atoms, alkoxyalkyl wherein the alkyl groups may be the same or different and contain from 1 to about 6 carbon atoms, substituted or unsubstituted phenyl, substituted or unsubstituted thiophenyl, or indole group, benzyl, phenethyl, 3,4-dimethoxyphenethyl, 1,1-dimethyl-2-(3-indolyl)-ethyl except that $R_1$ is not hydrogen when Y is $-SO_2R_1$, or $-COOR_1$; or a pharmaceutically acceptable salt thereof in a hydroalcoholic solution including from about 5% to about 50% ethanol by volume, 5% to about 50% by volume of a physiologically acceptable polyhydric compound; from about 0.05 to about 2 molar physiologically acceptable buffering agent; said hydroalcoholic solution having a pH of from about 2.0 to about 4.0.

4. A pharmaceutical composition useful in the treatment of cardiac conditions for parenteral administration comprising from about 0.01% to about 30% of a β-adrenergic blocking compound according to claim 1 of the formula

VI wherein $X_1$, $X_2$ and $X_3$ may be the same or different and represent hydrogen, halogen, hydroxy, nitro, amino, alkyl of from 1 to about 4 carbon atoms, or benzyloxy; W represents alkylene of from 1 to about 6 carbon atoms; and $R_1$ represents alkyl of from 1 to about 6 carbon atoms, alkoxyalkyl wherein the alkyl groups may be the same or different and contain from 1 to about 4 carbon atoms, cycloalkyl of from 3 to about 8 carbon atoms, phenyl, benzyl, or a thiophenyl, or indole group; or a pharmaceutically acceptable salt thereof in a hydroalcoholic solution including from about 5% to about 50% ethanol by volume, 5% to about 50% by volume of a physiologically acceptable polyhydric compound; from about 0.05 to about 2 molar physiologically acceptable buffering agent; said hydroalcoholic solution having a pH of from about 2.0 to about 4.0.

5. A pharmaceutical composition useful in the treatment of cardiac conditions for parenteral administration comprising from about 0.01% to about 30% of a β-adrenergic blocking compound according to claim 1 of the formula

VII wherein $X_1$, $X_2$ and $X_3$ may be the same or different and represent hydrogen, halogen, hydroxy, nitro, amino, alkyl of from 1 to about 4 carbon atoms, or benzyloxy; A represents alkylene of from 1 to about 6 carbon atoms; and $R_1$ and $R_3$ may be the same or different and represent hydrogen, alkyl of from 1 to about 6 carbon atoms, alkoxyalkyl wherein the alkyl groups may be the same or different and contain from 1 to about 4 carbon atoms, cycloalkyl of from 3 to about 8 carbon atoms, phenyl, or benzyl; or a pharmaceutically acceptable salt thereof in a hydroalcoholic solution including from about 5% to about 50% ethanol by volume, 5% to about 50% by volume of a physiologically acceptable polyhydric compound; from about 0.05 to about 2 molar physiologically acceptable buffering agent; said hydroalcoholic solution having a pH of from about 2 to about 4.0.

6. A pharmaceutical composition useful in the treatment of cardiac conditions for parenteral administration comprising from about 0.01% to about 30% of a β-adrenergic blocking compound according to claim 1 of the formula

VIII wherein $X_1$, $X_2$ and $X_3$ may be the same or different and represent hydrogen, halogen, hydroxy, nitro, amino, alkyl of from 1 to about 4 carbon atoms, or benzyloxy; W represents alkylene of from 1 to about 6 carbon atoms; and $R_1$ represents alkyl of from 1 to about 6 carbon atoms, alkoxyalkyl wherein the alkyl groups may be the same or different and contain from 1 to about 4 carbon atoms, cycloalkyl of from 3 to about 8 carbon atoms, phenyl, benzyl, or a thiophenyl, or indole group; or a pharmaceutically acceptable salt thereof in a hydroalcoholic solution including from about 5% to about 50% ethanol by volume, 5% to about 50% by volume of a physiologically acceptable polyhydric compound; from about 0.05 to about 2 molar physiologically acceptable buffering agent; said hydroalcoholic solution having a pH of from about 2.0 to about 4.0.

7. A pharmaceutical composition useful in the treatment of cardiac conditions for parenteral administration comprising from about 0.01% to about 30% of a β-adrenergic blocking compound according to claim 1 of the formula wherein $X_1$, $X_2$ and $X_3$ may be the same or different and represent hydrogen, halogen, hydroxy, nitro, amino, alkyl of from 1 to about 4 carbon atoms, or benzyloxy; W represents alkylene of from 1 to about 6 carbon atoms; and $R_1$ and $R_3$ may be the same or different and represent hydrogen, alkyl of from 1 to about 6 carbon atoms, alkoxyalkyl wherein the alkyl groups may be the same or different and contain from 1 to about 4 carbon atoms, cycloalkyl of from 3 to about 8 carbon atoms, phenyl, benzyl; or a pharmaceutically acceptable salt thereof in a hydroalcoholic solution including from about 5% to about 50% ethanol by volume, 5% to about 50% by volume of a physiologically acceptable polyhydric compound; from about 0.05 to about 2 molar physiological acceptable buffering agent; said hydroalcoholic solution having a pH of from about 2.0 to about 4.0.

8. A pharmaceutical composition useful in the treatment of cardiac conditions for parenteral administration comprising from about 0.01% to about 30% of a β-adrenergic blocking compound according to claim 1 of the formula wherein $X_1$, $X_2$ and $X_3$ may be the same or different and represent hydrogen, halogen, hydroxy, nitro, amino, alkyl of from 1 to about 4 carbon atoms, or benzyloxy; W represent alkylene of from 1 to about 6 carbon atoms; and $R_1$ represents alkyl of from 1 to about 6 carbon atoms, alkoxyalkyl wherein the alkyl groups may be the same or different and contain from 1 to about 4 carbon atoms; or a pharmaceutically acceptable salt thereof in a hydroalcoholic solution including from about 5% to about 50% ethanol by volume, 5% to about 50% by volume of a physiologically acceptable polyhydric compound; from about 0.05 to about 2 molar physiologically acceptable buffering agent; said hydroalcoholic solution having a pH of from about 2.0 to about 4.0.

9. A pharmaceutical composition according to claim 1 wherein the compound is selected from the group consisting of 3-[2-(isopropylcarbonylamino)ethyl]amino-2-hydroxypropyl 2-fluorobenzoate, 3-[2-isopropylcarbonylamino)ethyl]amino-2-hydroxypropyl 2-fluorobenzoate hydrochloride, 3-[2-(benzylcarbonylamino)ethyl]amino-2-hydroxypropyl 2-fluorobenzoate, 3-[2(benzylcarbonylaminoethyl]amino-2-hydroxypropyl 2-fluorobenzoate hydrochloride, 3-[1-methyl-2-(methylcaarbonylamino)]-ethylamino-2-hydroxypropyl 2-fluorobenzoate, 3-[1,1-dimethyl-2-(methylcarbonylamino)]ethylamino-2-hydroxypropyl 2-fluorobenzoate, 3-[1,1-dimethyl-2-(isopropylcarbonylamino)]ethylamino-2-hydroxypropyl 2-fluorobenzoate, 3-[1,1-dimethyl-2-(cyclohexylcarbonylamino)ethyl]amino-2-hydroxypropyl 2-fluorobenzoate, 3-[1,1-dimethyl-2-(benzylcarbonylamino)]ethylamino-2-hydroxypropyl 2-fluorobenzoate, 3-[1,1-dimethyl-2-(benzylcarbonylamino)]ethylamino-2-hydroxypropyl 2-fluorobenzotee hydrochloride, 3-[1,1-dimethyl-2-(phenylsulfonylamino]ethylamino-2-hydroxypropyl 2-fluorobenzoate, 3-[1,1-dimethyl-2-(ethoxycarbonylamino)]ethylamino-2-hydroxypropyl 2-fluorobenzoate, 3-[1,1-dimethyl-2-(ethoxycarbonylamino)]ethylamino-2-hydroxypropyl 2-fluorobenzoate hydrochloride, 3-[1,1-dimethyl-2-[(2-methoxy)ethoxycarbonylamino]]ethylamino-2-hydroxypropyl 2-fluorobenzoate, and 3-[1,1-dimethyl-2-(dimethylaminosulfonylamino)]ethylamino-2-hydroxypropyl 2-fluorobenzoate.

10. The pharmaceutical composition of claim 9 wherein the polyhydric compound is selected from the group consisting of ethylene glycol, propylene glycol, glycerol, polyethylene glycol having a molecular weight of from about 200 to about 600 daltons, and glycerin; and the buffering agent comprises a tartrate buffer, an acetate buffer, trishydroxymethylaminomethane, glycine or cystine.

11. The pharmaceutical composition of claim 10 wherein the blocker of adrenergic β-receptors comprises from about 0.01% to about 10%, and the pH is from about 2.8 to about 3.2.

12. A pharmaceutical composition according to claim 1 wherein the compound is 3-[1,1-dimethyl-2-(aminocarbonylamino)ethyl]amino-2-hydroxypropyl 2-fluorobenzoate.

13. A pharmaceutical composition according to claim 1 wherein the compound is 3-[1,1-dimethyl-2-(methylaminocarbonylamino)]ethylamino-2-hydroxypropyl 2-fluorobenzoate.

14. A pharmaceutical composition according to claim 1 wherein the compound is 3-[1,1-dimethyl-2-(phenylaminocarbonylamino)]ethylamino-2-hydroxypropyl 2-fluorobenzoate.

15. A pharmaceutical composition useful in the treatment of cardiac conditions for parenteral administration comprising from about 0.01% to about 30% of a β-adrenergic blocking compound of the formula wherein Ar represents phenyl which is unsubstituted or substituted with alkyl of from 1 to about 6 carbon atoms, alkoxy wherein the alkyl group contains from 1 to about 4 carbon atoms, halogen, hydroxy, nitro, amino, phenoxy, or benzyloxy; W represents alkylene of from 1 to about 6 carbon atoms; and B represents $-NR_2COR_1$, $-NR_2CONR_1R_3$, $-NR_2SO_2R_1$, $-NR_2SO_2NR_1R_3$, or $NR_2COOR_1$, wherein $R_1$, $R_2$ and $R_3$ may be the same or different and represent hydrogen, alkyl of from 1 to about 6 carbon atoms, alkoxyalkyl wherein the alkyl group may be the same or different and contain from 1 to about 6 carbon atoms, cycloalkyl of from 3 to about 8 carbon atoms, a substituted or unsubstituted aryl group of from 5 to about 6 carbon atoms, except that $R_1$ is not hydrogen when B is $-NR_2SO_2R_1$ or $-NR_2COOR_1$; or a pharmaceutically acceptable salt thereof in a hydroalcoholic solution including from about 5 to about 50% ethanol by volume, 5% to about 50% by volume of a physiologically acceptable buffering agent; said hydroalcoholic solution having a pH of from about 2.0 to about 4.0.

16. A pharmaceutical composition useful as a blocker of adrenergic β-receptors in the treatment of cardiac conditions comprising a therapeutically effective amount of a compound of the formula

VII wherein $X_1$ is hydrogen, $X_2$ is hydrogen, $X_3$ is fluoro, W is $-C(CH_3)_2CH_2-$, $R_1$ is hydrogen, and $R_3$ is hydrogen, lower alkyl or phenyl, or a pharmaceutically acceptable salt thereof, and a pharmaceutically acceptable carrier suitable for parenteral administration.

17. The pharmaceutical composition of claim 16 wherein the blocker of adrenergic β-receptors comprises from about 0.01% to about 30% by weight of the composition in a hydroalcoholic solution; and the pharmaceutically acceptable carrier comprises a hydroalcoholic solution including from about 5% to about 50% ethanol by volume, from about 5% to about 50% of a polyhydric compound, from about 0.05 to about 2 molar concentration of a buffering agent, said hydroalcoholic solution having a pH of from about 2.0 to about 4.0.

18. The pharmaceutical composition of claim 17 wherein the polyhydric compound is selected from the group consisting of ethylene glycol, propylene glycol, glycerol, polyethylene glycol having a molecular weight of from about 200 to about 600 daltons, and glycerin; and the buffering agent comprises a tartrate buffer, an acetate buffer, trishydroxymethylaminomethane, glycine or cystine.

19. The pharmaceutical composition of claim 18 wherein the blocker of adrenergic β-receptors comprises from about 0.01% to about 10%, and the pH is from about 2.8 to about 3.2.

20. The pharmaceutical composition of claim 19 wherein the polyhydric compound is propylene glycol and the volume ratio of ethanol to propylene glycol is 1:1.

21. The pharmaceutical composition of claim 20 wherein the ratio of β-adrenergic blocking compound to buffering agent is 1:1 to 3:1.

22. The pharmaceutical composition of claim 21 wherein the β-adrenergic blocking compound is an l-isomer.

23. The pharmaceutical composition of claim 21 wherein $X_1$ is hydrogen, $X_2$ is hydrogen, $X_3$ is fluoro, W is $-C(CH_3)_2CH_2$), $R_1$ is hydrogen, and $R_3$ is hydrogen.

24. The pharmaceutical composition of claim 23 wherein said compound is an l-isomer.

25. The pharmaceutical composition of claim 21 wherein $X_1$ is hydrogen, $X_2$ is hydrogen, $X_3$ is fluoro, W is $-C(CH_3)_2CH_2-$, $R_1$ is hydrogen, and $R_3$ is methyl.

26. The pharmaceutical composition of claim 25 wherein said compound is an l-isomer.

27. The pharmaceutical composition of claim 21 wherein $X_1$ is hydrogen, $X_2$ is hydrogen, $X_3$ is fluoro, W is $-C(CH_3)_2CH_2-$, $R_1$ is hydrogen, and $R_3$ is phenyl.

28. The pharmaceutical composition of claim 27 wherein said compound is an l-isomer.

29. The pharmaceutical composition of claim 16 wherein said compound is an l-isomer.

30. A pharmaceutical composition useful as a blocker of adrenergic β-receptors in the treatment of cardiac conditions comprising a therapeutically effective amount of a compound of the formula

VI wherein $X_1$ is hydrogen, methyl, hydroxy or amino; $X_2$ is hydrogen or hydroxy; $X_3$ is hydrogen, chloro or fluoro; W is $-C(CH_3)_2CH_2-$ or $-C(CH_3)_2CH_2-$; and $R_1$ is or a pharmaceutically acceptable salt thereof, and a pharmaceutically acceptable carrier suitable for parenteral administration.

31. The pharmaceutical composition of claim 30 wherein the blocker of adrenergic β-receptors comprises from about 0.01% to about 30% by weight of the composition in a hydroalcoholic solution; and the pharmaceutically acceptable carrier comprises a hydroalcoholic solution including from about 5% to about 50% ethanol by volume; from about 5% to about 50% by volume of a polyhydric compound; from about 0.05% to about 2 mole concentration of a buffering agent; said hydroalcoholic solution having a pH of from about 2.0 to about 4.0.

32. The pharmaceutical composition of claim 31 wherein the polyhydric compound is selected from the group consisting of ethylene glycol, propylene glycol, glycerol, polyethylene glycol having a molecular weight of from about 200 to about 600 daltons, are glycerin; and the buffering agent comprises a tartrate buffer, an acetate buffer, trishydroxymethylaminomethane, glycine or cystine.

33. The pharmaceutical composition of claim 32 wherein the blocker of adrenergic β-receptors comprises from about 0.01% to about 10%, and the pH is from about 2.8 to about 3.2.

34. The pharmaceutical composition of claim 33 wherein the polyhydric compound is propylene glycol and the volume ratio of ethanol to propylene glycol is 1:1.

35. The pharmaceutical composition of claim 34 wherein the ratio of β-adrenergic blocking compound to buffering agent is 1:1 to 3:1.

* * * * *